US00PP13841P29

(12) United States Plant Patent
den Haan

(10) Patent No.: US PP13,841 P2
(45) Date of Patent: May 20, 2003

(54) ORIGANUM PLANT NAMED 'ZORBA RED'

(76) Inventor: Pieter den Haan, Korteind 3, 4651 PE Steenbergen (NL)

( * ) Notice: Subject to any disclaimer, the term of this patent is extended or adjusted under 35 U.S.C. 154(b) by 0 days.

(21) Appl. No.: 10/171,831

(22) Filed: Jun. 17, 2002

(51) Int. Cl.[7] ..... A01H 5/00
(52) U.S. Cl. ..... Plt./258

(58) Field of Search ..... Plt./258

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Origanum plant named 'Zorba Red', characterized by its compact and low spreading plant habit; freely branching growth habit; aromatic dark green foliage; and white-colored flowers subtended by red purple-colored bracts.

1 Drawing Sheet

BOTANICAL CLASSIFICATION

*Origanum vulgare* cultivar Zorba Red.

BACKGROUND OF THE INVENTION

The present Invention relates to a new and distinct cultivar of Origanum plant, botanically known as *Origanum vulgare*, and hereinafter referred to by the name 'Zorba Red'.

The new Origanum is a product of a planned breeding program conducted by the Inventor in Steenbergen, The Netherlands. The objective of the breeding program is to create new compact Origanums with unique flower coloration.

The new Origanum is a naturally-occurring whole plant mutation of a proprietary selection of *Origanum vulgare* identified as PH96, not patented. The new Origanum was discovered and selected as a single plant within a population of plants of the selection PH96 in 1997 in a controlled environment in Steenbergen, The Netherlands. The new Origanum was selected on the basis of its compact plant habit and white-colored flowers and red purple-colored flower bracts.

Asexual reproduction of the new cultivar by terminal cuttings taken in a controlled environment in Steenbergen, The Netherlands since 1997, has shown that the unique features of this new Origanum are stable and reproduced true to type in successive generations.

SUMMARY OF THE INVENTION

Plants of the cultivar 'Zorba Red' have not been observed under all possible environmental conditions. The phenotype may vary somewhat with variations in environment and culture such as temperature, light intensity, and daylength without, however, any variance in genotype.

The following traits have been repeatedly observed and are determined to be the unique characteristics of 'Zorba Red'. These characteristics in combination distinguish 'Zorba Red' as a new and distinct cultivar:

1. Compact and low spreading plant habit.
2. Freely branching growth habit.
3. Aromatic dark green foliage.

4. White-colored flowers subtended by red purple-colored bracts.

Plants of the new Origanum differ from plants of the parent selection primarily in plant habit as plants of the new Origanum are much more compact. In addition, flowers of plants of the new Origanum are more conspicuous than flowers of plants of the selection PH96.

Plants of the new Origanum differ from plants of the cultivar 4839, U.S. Plant patent application Ser. No. 10/171,835, primarily in flower bract color as plants of the cultivar 4839 have light green-colored flower bracts.

Plants of the new Origanum can be compared to plants of the cultivar Rosenkuppel, not patented. In side-by-side comparisons conducted in Steenbergen, The Netherlands, plants of the new Origanum and the cultivar Rosenkuppel differed in the following characteristics:

1. Plants of the new Origanum were more vigorous than plants of the cultivar Rosenkuppel.
2. Plants of the new Origanum had dark green-colored leaves whereas plants of the cultivar Rosenkuppel had brownish green-colored leaves.
3. Flower bracts of plants of the new Origanum were brighter in color than flower bracts of plants of the cultivar Rosenkuppel.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Origanum. The photograph comprises a side perspective view of a typical flowering plant of 'Zorba Red'.

DETAILED BOTANICAL DESCRIPTION

In the following description, color references are made to The Royal Horticultural Society Colour Chart except where general terms of ordinary dictionary significance are used. Plants grown for 12-weeks in 15-cm containers were used for the photographs and following description. Plants were grown in a polycarbonate-covered greenhouse in Lompoc, Calif. during the late winter/early spring with day temperatures ranging from 18 to 24° C., night temperatures ranging from 16 to 18° C., and light levels ranging from 4,000 to 8,000 foot-candles.

Botanical classification: *Origanum vulgare* cultivar 'Zorba Red'.

Parentage: Naturally-occurring whole plant mutation of proprietary selection of *Origanum vulgare* identified as PH96, not patented.

Propagation:

*Type cutting.*—Terminal cuttings.

*Time to initiate roots.*—About 10 days at 18° C.

*Time to develop roots.*—About 20 days at 18° C.

*Root description.*—Fibrous.

*Rooting habit.*—Freely branching.

Plant description:

*Form.*—Compact and low spreading growth habit. Lateral branches initially upright, but tend to cascade with subsequent development. Freely branching with about 18 lateral branches. Vigorous.

*Plant height.*—About 32 cm.

*Plant diameter.*—About 73 cm.

*Lateral branches.*—Length: About 52 cm. Diameter: About 4 mm. Internode length: Vegetative branches: About 2.5 cm. Flowering branches: About 5.5 cm. Strength: Moderately strong. Texture: Fine pubescence. Color: Ground color, 147C overlain with anthocyanin, 182B to 59A.

*Foliage description.*—Arrangement: Opposite, simple. Quantity per lateral branch: About 26. Length: About 3.4 cm. Width: About 2.3 cm. Shape: Rounded elliptic. Apex: Rounded. Base: Acute. Margin: Entire. Texture: Upper surface: Glabrous; glandular. Lower surface: Pubescent; glandular. Venation pattern: Arcuate. Fragrance: Aromatic, sweet herb-like. Petiole length: About 1.8 cm. Petiole diameter: About 2 mm. Color: Young foliage, upper surface: 138A. Young foliage, lower surface: 144A. Mature foliage, upper surface: 147A. Mature foliage, lower surface: 147B. Venation, upper surface: 147C. Venation, lower surface: 147D. Petiole: 146D.

Flower description:

*Flower type and habit.*—Small single bilabiate flowers arranged in terminal and axillary panicles; individual flowers face upward or outward depending on position in the panicle. Freely flowering; more than 250 flowers and flower buds per flowering branch. Flowers not persistent.

*Natural flowering season.*—Summer and fall, flowering continuous during this period.

*Flower longevity on the plant.*—About 4 to 7 days.

*Fragrance.*—Not detected.

*Terminal panicle height.*—About 3.8 cm.

*Terminal panicle diameter.*—About 5 cm.

*Flowers.*—Appearance: Zygomorphic; bilabiate. Length: About 5 mm. Diameter: About 4 mm. Depth: About 6 mm.

*Flower buds* (*showing color*).—Length: About 4 mm. Diameter: About 2 mm. Shape: Elongated ovoid. Color: 155C.

*Corolla.*—Petal arrangement/appearance: Bilabiate; five petals, upper two petals fused at base and lower three petals fused at base. Petal length: Upper petals: About 2 mm. Lower petals: About 3 mm. Petal width: Upper petals: About 2 mm. Lower petals: About 4 mm. Petal shape: Roughly oval. Petal apex: Rounded. Petal margin: Entire. Petal texture: Smooth, satiny. Petal color: Upper and lower surfaces, when opening: 155D. Upper and lower surfaces, fully opened: More white than 155D.

*Calyx.*—Quantity/arrangement: One single calyx tube per flower; five fused sepals. Length: About 3 mm. Diameter: About 2 mm. Shape: Tubular or cup-shaped. Apex: Acute. Texture: Slightly pubescent. Color: Immature, upper and lower surfaces: 144C. Mature, upper surface: 144C. Mature, lower surface: 144C; at apices, 59A.

*Bracts.*—Quantity/arrangement: One bract subtends each flower. Length: About 6 mm. Diameter: About 4 mm. Shape: Elongated ovate. Color, upper and lower surfaces: Ground color, 59A; at base, 144C.

*Peduncles.*—Length: About 3.75 cm. Diameter: About 1.5 mm. Strength: Strong. Angle: Terminals, erect; axillary, about 45° from vertical. Color: 183A to 183B.

*Pedicels.*—Length: About 1 mm. Diameter: Less than 1 mm. Strength: Moderately strong. Angle: Terminals, erect; axillary, about 45° from vertical. Color: 144C.

*Reproductive organs.*—Stamens: Quantity: Four per flower. Anther shape: Ovoid. Anther length: Less than 1 mm. Anther color: 155D. Pollen amount: None. Pistils: Quantity: One per flower. Pistil length: About 7 mm. Stigma shape: Forked. Stigma color: 55D. Style length: About 6 mm. Style color: 55D. Ovary color: 144D.

*Seed/fruit.*—Seed nor fruit production has not been observed.

Disease/pest resistance: Plants of the new Origanum have not been noted to be resistant to pathogens or pests common to Origanum.

Weather tolerance: Plants of the new Origanum have been observed to be tolerant to rain, wind and temperatures ranging from 1 to 30° C.

I claim:

1. A new and distinct cultivar of Origanum plant named 'Zorba Red', as illustrated and described.

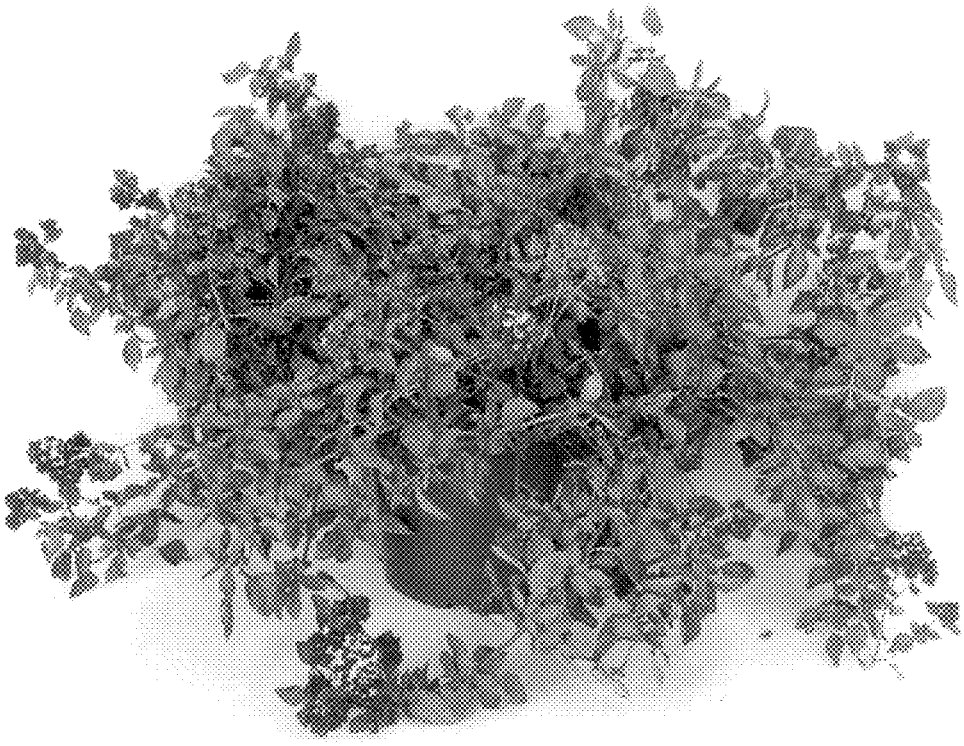

* * * * *